United States Patent [19]

Holtkamp

[11] Plant 4,433

[45] Jul. 10, 1979

[54] AFRICAN VIOLET PLANT

[75] Inventor: Reinhold Holtkamp, Isselburg, Fed. Rep. of Germany

[73] Assignee: Gesellschaftsvertrag uber die Erfindergemeinschaft "OPTIMARA", Isselburg, Fed. Rep. of Germany

[21] Appl. No.: 880,050

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill
*Attorney, Agent, or Firm*—Donald D. Jeffery

[57] ABSTRACT

An African violet named Minnesota having large star-shaped, non-dropping red-purple flowers, strong upright flower stems, with 5–7 flowers on each stem and 10–12 stems on each plant, dark green leaves, and vigorous growth habit.

1 Drawing Figure

The present invention comprises a new and distinct cultivar of African violet plant, botanically known as *Saintpaulia ionantha,* and referred to by the cultivar name Minnesota. Minnesota was referred to during the breeding and selection process by the numbers 123/1–74/77, and is principally characterized by its large red-purple, star-shaped, non-dropping flowers, strong upright flower stems, and dark green foliage.

The new cultivar was originated from a cross made in a controlled breeding program in Isselburg, Rhineland, Germany. The female, or seed parent was F-I pink frilled, an unpatented cultivar. The male, or pollen parent is also unpatented and identified by the number XIX 4395.

Minnesota was discovered and selected as a flowering plant within the porgeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Minnesota, which in combination distinguish this African violet as a new and distinct cultivar:

(1) Very large star-shaped flowers, red-purple in color, with wavy edges.

(2) Strong upright flower stems.

(3) 5–7 flowers on each flower stem.

(4) 10–12 flower stems on each plant.

(5) Dark-green leaves, with the underside of the leaves being red.

(6) Flowers will not drop.

(7) Very vigorous growth habit.

The accompanying photographic drawing shows a typical specimen plant of the new cultivar. The colors appearing in the photograph are as true as possible with color illustrations of this type.

In the following description, flower color value are referenced to Horticultural Color Chart (Wilson), and the color values of foliage, buds, sepals, and reproductive organs are referenced to RHS Color Chart, 1966 edition. It is noted that it was difficult to obtain exact color values for the flowers, and the color values indicated below are as accurate as possible.

Botanical classification: *Saintpaulia ionantha,* Ramat cv Minnesota.

Parentage:

*Male parent.*—XIX 4395.

*Female parent.*—FI pink frilled.

Propagation: The new cultivar holds its distinguishing characteristics through successive propagations by leaf cuttings and by division of shoots.

Plant: From 9 cm. to 10 cm. tall when grown in pots, and approximately 30 cm. in diameter when fully grown.

*Leaves.*—General form: Oblong. Diameter: 55 mm. Texture: tender, velvety. Aspect: dark green, edges of leaves slightly serrated. Veins: pronounced. Color (upperside): 131 A, with the photograph showing the leaves lighter than their true color. Color (underside): 59 B .Petiole: reddish brown.

Flowers:

*Buds.*—Round, 8–9 mm. in diameter, color 62 C.

*Sepals.*—Five, 6–7 mm. long, spear-shaped. Color: 187 B. Calyx: funnel-shaped. Aspect: flower stem and receptacle are connected. Peduncle: straight, up to 25 mm. long.

Individual flowers:

*Size.*—45–50 mm. in total flower diameter, each petal being 23–25 mm. long and 20 mm. wide.

*Color.*—Upperside: slightly darker than 732 (Doge Purple). Underside: 732/1 to 732/2.

*Borne.*—Up to 7 flowers on each flower stem.

*Shape.*—Star-shaped, five petals of equal size, having wavy edges.

*Arrangement.*—Strong upright flower stems, with up to 7 flowers on short peduncles.

*Flowering time.*—8–10 weeks after potting, the first flowers will show; 10–12 weeks after potting, the plant is in full bloom.

Reproductive organs:

*Stamens.*—4–5 stamens, close together.

*Anthers.*—8–10 anthers, color 7 A.

*Arrangement.*—The stamens are connected to the receptacle by filaments and are positioned around the seed vessel.

*Filaments.*—3–5 mm. long.

*Styles.*—8 mm. long, color 61 A.

*Pollen color.*—7 C.

Roots: Well developed and spreading; the young roots are white, the older ones are brownish.

Disease resistance: No disease problem noticed to date.

General Observations: Minnesota is a very vigorous growing African violet with very large dark red-purple flowers of star-shape. 8 weeks after potting, the first flowers show, and the flowers do not drop. On each flower stem, there are up to seven large flowers on short peduncles. The leaves are dark green and their edges are slightly serrated.

I claim:

1. A new and distinct cultivar of African violet known by the cultivar name Minnesota and characterized by the combined features of large-star-shaped, non-dropping red-purple flowers, strong upright flower stems, with 5–7 flowers on each stem and 10–12 stems on each plant, dark green leaves, and vigorous growth habit.

* * * * *

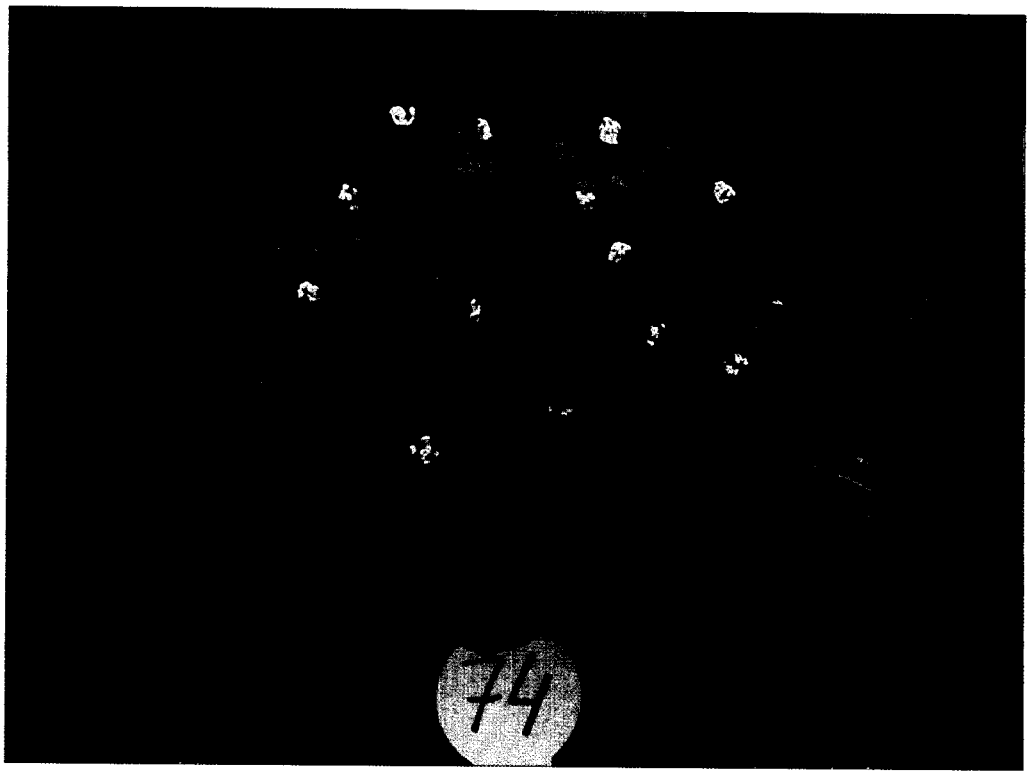
74